US009205183B2

(12) United States Patent
Hartwell et al.

(10) Patent No.: US 9,205,183 B2
(45) Date of Patent: Dec. 8, 2015

(54) FLUID COLLECTION

(75) Inventors: Edward Yerbury Hartwell, Hull (GB); Jonathan Chappel, York (GB); Neill Philip Bannister, Holme on Spalding Moor (GB)

(73) Assignee: Smith & Nephew PLC, London (GB)

( * ) Notice: Subject to any disclaimer, the term of this patent is extended or adjusted under 35 U.S.C. 154(b) by 839 days.

(21) Appl. No.: 12/918,202

(22) PCT Filed: Feb. 27, 2009

(86) PCT No.: PCT/GB2009/050200
§ 371 (c)(1),
(2), (4) Date: Mar. 28, 2011

(87) PCT Pub. No.: WO2009/106895
PCT Pub. Date: Sep. 3, 2009

(65) Prior Publication Data
US 2011/0172616 A1    Jul. 14, 2011

(30) Foreign Application Priority Data
Feb. 27, 2008   (GB) .................................. 0803564.4

(51) Int. Cl.
| *A61M 1/00* | (2006.01) |
| *A61M 5/178* | (2006.01) |
| *A61M 5/00* | (2006.01) |
| *A61M 5/32* | (2006.01) |
| *A61M 35/00* | (2006.01) |
| *A61F 13/00* | (2006.01) |

(52) U.S. Cl.
CPC ........... *A61M 1/0003* (2013.01); *A61M 1/0001* (2013.01); *A61M 1/0019* (2013.01); *A61M 1/0088* (2013.01)

(58) Field of Classification Search
CPC ......... A61M 1/00; A61M 5/178; A61M 5/00; A61M 5/32; A61M 35/00; A61F 13/00
USPC ........................................................ 604/319
See application file for complete search history.

(56) References Cited

U.S. PATENT DOCUMENTS 2,468,445 A * 4/1949 Hurst ............................ 604/397
3,572,340 A   3/1971 Lloyd et al.
(Continued)

FOREIGN PATENT DOCUMENTS

EP      0923905 A   6/1999
WO     WO 87/00439    *  1/1987  .............. A61M 1/00
(Continued)

OTHER PUBLICATIONS

International Search Report for PCT/GB2009/050200 (SMNPH.115APC) mailed Jun. 5, 2009.
(Continued)

*Primary Examiner* — Tatyana Zalukaeva
*Assistant Examiner* — Ilya Treyger
(74) *Attorney, Agent, or Firm* — Knobbe, Martens, Olson & Bear, LLP

(57) ABSTRACT

An apparatus and method for collecting fluid are disclosed. The apparatus includes a body portion comprising a fluid inlet and an outlet, an expandable container secured to the body portion, at least one wicking element extending from within the body portion into the container, and at least one super absorber element arranged inside the container.

17 Claims, 2 Drawing Sheets

(56) References Cited

U.S. PATENT DOCUMENTS

| | | | |
|---|---|---|---|
| 5,458,586 | A | 10/1995 | Adiletta |
| 6,648,862 | B2 * | 11/2003 | Watson .................. 604/319 |
| 7,615,036 | B2 | 11/2009 | Joshi et al. |
| 7,779,625 | B2 | 8/2010 | Joshi et al. |
| 7,964,766 | B2 | 6/2011 | Blott et al. |
| 8,007,481 | B2 | 8/2011 | Schuessler et al. |
| 8,048,046 | B2 | 11/2011 | Hudspeth et al. |
| 8,080,702 | B2 | 12/2011 | Blott et al. |
| 8,118,794 | B2 | 2/2012 | Weston |
| 8,177,763 | B2 | 5/2012 | Wiesner |
| 8,216,198 | B2 | 7/2012 | Heagle et al. |
| 8,251,979 | B2 | 8/2012 | Malhi |
| 8,257,328 | B2 | 9/2012 | Augustine et al. |
| 8,303,552 | B2 | 11/2012 | Weston |
| 8,303,555 | B2 * | 11/2012 | Miau et al. .................. 604/321 |
| 8,333,744 | B2 | 12/2012 | Hartwell et al. |
| 8,414,519 | B2 | 4/2013 | Hudspeth et al. |
| 8,460,255 | B2 | 6/2013 | Joshi et al. |
| 8,551,060 | B2 | 10/2013 | Schuessler et al. |
| 8,551,061 | B2 | 10/2013 | Hartwell |
| 8,568,386 | B2 | 10/2013 | Malhi |
| 8,569,566 | B2 | 10/2013 | Blott et al. |
| 8,622,981 | B2 | 1/2014 | Hartwell et al. |
| 8,679,081 | B2 | 3/2014 | Heagle et al. |
| 8,834,452 | B2 | 9/2014 | Hudspeth et al. |
| 2004/0006321 | A1 | 1/2004 | Cheng et al. |
| 2006/0280650 | A1 | 12/2006 | Wong et al. |
| 2008/0082059 | A1 | 4/2008 | Fink et al. |
| 2008/0108977 | A1 | 5/2008 | Heaton et al. |
| 2009/0292263 | A1 * | 11/2009 | Hudspeth et al. .................. 604/313 |
| 2010/0049150 | A1 | 2/2010 | Braga et al. |
| 2011/0071483 | A1 | 3/2011 | Gordon et al. |
| 2011/0087178 | A2 | 4/2011 | Weston |
| 2011/0251567 | A1 | 10/2011 | Blott et al. |
| 2011/0275964 | A1 | 11/2011 | Greener |
| 2012/0046626 | A1 | 2/2012 | Sanders et al. |
| 2012/0053543 | A1 | 3/2012 | Miau et al. |
| 2012/0265160 | A1 | 10/2012 | Wiesner |
| 2013/0144235 | A1 | 6/2013 | Augustine et al. |
| 2013/0190705 | A1 | 7/2013 | Vess et al. |
| 2014/0100538 | A1 | 4/2014 | Hartwell |
| 2014/0107598 | A1 | 4/2014 | Wudyka |
| 2014/0128822 | A1 | 5/2014 | Malhi |
| 2014/0135718 | A1 | 5/2014 | Hartwell |
| 2014/0163491 | A1 | 6/2014 | Schuessler et al. |

FOREIGN PATENT DOCUMENTS

| | | |
|---|---|---|
| WO | WO 2009/002260 | 12/2008 |
| WO | WO 2009/151645 | 12/2009 |
| WO | WO 2010/039481 | 4/2010 |

OTHER PUBLICATIONS

U.S. Appl. No. 13/212,039, filed Aug. 17, 2011, Blott, et al.
U.S. Appl. No. 14/575,968, filed Dec. 18, 2014, Blott, et al.
U.S. Appl. No. 14/486,338, filed Sep. 15, 2014, Hudspeth, et al.
U.S. Appl. No. 13/912,716, filed Jun. 7, 2013, Joshi, et al.
U.S. Appl. No. 13/777,171, filed Feb. 26, 2013, Hudspeth et al.

* cited by examiner

FLUID COLLECTION

CROSS-REFERENCE TO RELATED APPLICATIONS

This application is a U.S. National Phase of the PCT International Application No. PCT/GB2009/050200 filed on Feb. 27, 2009, designating the United States and published on Sep. 3, 2009 as WO 2009/106895, and which claims priority to Great Britain Patent Application No. 0803564.4, filed Feb. 27, 2008. The disclosure of these prior applications is incorporated by reference in their entirety and should be considered a part of this specification.

BACKGROUND OF THE INVENTION

Field of the Invention

The present invention relates to a method and apparatus for trapping and collecting fluid. In particular, but not exclusively, the present invention provides an apparatus which can trap and store fluid removed as part of a medical procedure.

Suction pumps are sometimes used in the removal of fluid in medical procedures, for example, during topical negative pressure (TNP) wound therapy, closed suction, surgery and clearance of fluid from lungs etc. During pumping liquid such as wound exudate must be trapped and stored. Fluid traps for such suction pumps thus tend to be bulky even when empty since the container used to trap and collect fluid needs to be of a size suitably big to be useful over a period of time. The bulky fluid traps are not only costly to transport and manufacture but also are difficult to store. Also the relatively large size makes the containers difficult to conceal during use which may provide unsatisfactory to a user trying to carry on their normal life.

Current vacuum pump devices for wound drainage and negative pressure wound therapy (NPWT) often utilise bulky fluid collection canisters to trap the fluid removed from the body. Two types of fluid collection canister are well known, namely rigid canisters formed from a single wall rigid construction and so-called flexible canisters that sit inside a further rigid container. In these latter canisters the inner flexible container is disposable but a relatively large outer rigid body is still needed to protect and support the flexible container and this is prone to the problems noted above.

SUMMARY OF SOME EXEMPLIFYING EMBODIMENTS

It is an aim of the present invention to at least partly mitigate the above-mentioned problems.

It is an aim of embodiments of the present invention to provide apparatus which can trap and store fluid and which, when empty, is relatively small and discreet and yet which can expand to provide adequate capacity for the apparatus to be used over a prolonged period of time or when large quantities of liquid are generated.

It is an aim of embodiments of the present invention to provide a method and apparatus for trapping and collecting wound exudate from a wound or fluid from lungs during a medical procedure.

It is an aim of embodiments of the present invention to provide a method of trapping and collecting fluid utilising an expandable container which is able to absorb liquid under compression conditions. Even, for some embodiments, at compression pressures of up to 200 mmHg.

According to a first aspect of the present invention there is provided apparatus for collecting fluid, comprising:
a body portion comprising a fluid inlet and an outlet;
an expandable container secured to the body portion;
at least one wicking element extending from within the body portion into the container; and
at least one super absorber element arranged inside the container.

According to a second aspect of the present invention there is provided a method for collecting fluid, comprising the steps of:
applying a negative pressure at an outlet of an apparatus body portion to thereby draw liquid through an inlet of the body portion;
via at least one wicking element, trapping and transporting the drawn liquid away from the body portion into an expandable container secured to the body portion; and
absorbing the liquid in the container via at least one super absorber element, the container expanding as the super absorber expands.

Embodiments of the present invention provide a relatively small and compact apparatus and method for using the apparatus which is able to trap and collect fluid. Advantageously, but not exclusively, embodiments of the present invention can be used to trap and collect fluids removed during a medical procedure such as TNP, surgery or the like.

Embodiments of the present invention utilise a wicking material which receives liquid at one location close to an inlet to a body portion. The wicking material rapidly transports the liquid, via capillary action, to a super absorbent material which expands as more and more liquid is absorbed. A flexible and enlargeable container is utilised which expands as the super absorber material absorbs more and more liquid. The wicking material and super absorber prevent collapse of the container when a negative pressure is applied.

Embodiments of the present invention provide a flexible waste container which allows the apparatus to be accommodated on a person in a more user friendly manner. In an "empty" state the waste receptacle is significantly smaller in volume than an equivalent rigid container of fixed initial volume. This reduces transport and storage requirements and reduces the volume in use. This is particularly advantageous as it will be appreciated that conventional canisters used for trapping and containing fluids spend a majority of their life in use in an empty/part empty state.

BRIEF DESCRIPTION OF THE DRAWINGS

Embodiments of the present invention will now be described hereinafter, by way of example only, with reference to the accompanying drawings in which.

DETAILED DESCRIPTION OF SOME EXEMPLIFYING EMBODIMENTS

Figure 1:
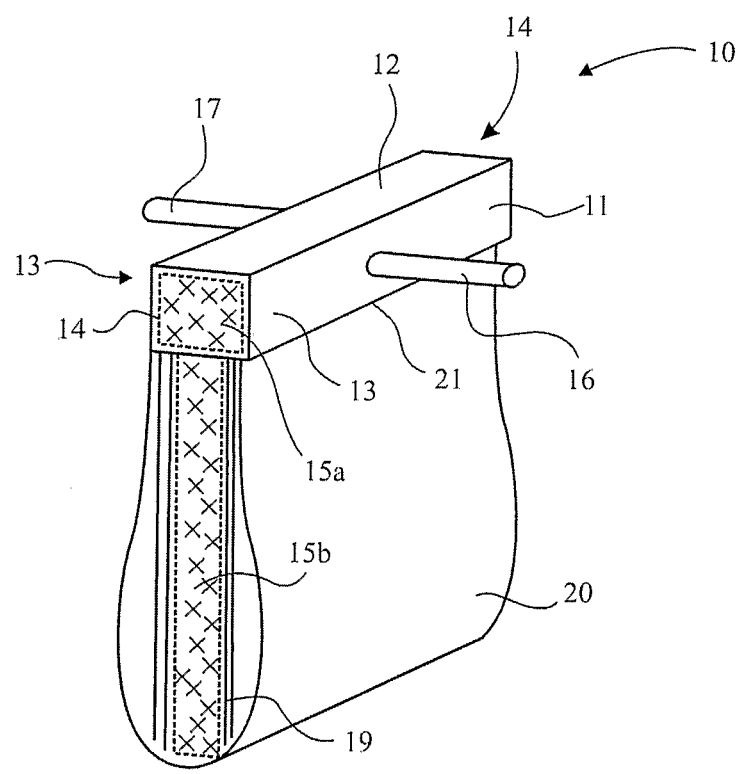
FIG. 1 illustrates apparatus for collecting fluid.

In the drawings like reference numerals refer to like parts.
FIG. 1 illustrates a fluid trap 10 according to an embodiment of the present invention. Throughout this specification reference is made to the trapping and holding or storing of fluid. It is to be understood that the trapping process encapsulates the concept of at least partially removing fluid from a flow path whilst the storing/containing aspect refers to the storage of trapped fluid, again away from a fluid path. As illustrated in FIG. 1 the apparatus 10 includes an upper body 11 which is rigid or semi-rigid and may be formed from metal or a plastics material or the like. As illustrated in FIG. 1, the body 11 is a box-like container formed as a paralleliped with an upper substantially rectangular side wall 12 and rectangular side walls 13. Substantially square side walls 14 close the open ends of the paralleliped. It is to be noted that other shapes may be adopted for the body in accordance with further embodiments of the present invention.

It is also to be noted that the front end 14 shown in FIG. 1 is shown cut away to reveal how a mass of wicking material 15 is used to fill the inside of the box-like body 11.

The wicking material 15 includes an upper portion 15a which fills the inside of the body 11 and an elongate portion 15b extending downwardly from the upper portion. The wicking material forming the upper and lower parts of the wick can be formed from any material which may be used to transport liquid via capillary action. For example, cotton gauze, non-woven polyester or the like. A fluid inlet 16 and fluid outlet 17 are provided in the body 11. The fluid inlet 16 allows fluid, from a target location where fluid is to be removed, to be drawn into the fluid trap 10. The fluid outlet 17 is utilised to remove a gaseous part of the input fluid when a negative pressure, provided by a pump or the like, is applied. Effectively fluid is thus sucked through the fluid inlet and outlet. The upper portion of the wicking material 15 is used to trap the liquid part of the pumped fluid and capillary action draws the trapped liquid away from the body 11 in a downwardly direction. The liquid is absorbed by super absorbent material 19 formed as sheets in the dry state. It will be appreciated that in the dry state the superabsorber may alternatively or additionally be provided in a powdered or granular form. A flexible container 20 is sealed at its upper edge 21 to a lower region of the fluid trap body 11. The flexible container 20 can expand as more and more liquid is absorbed by the super absorber 19 during fluid removal. Thus in an initial dry state prior to fluid removal the overall apparatus is relatively small and compact. This makes the apparatus easy to store and transport.

Figure 2:
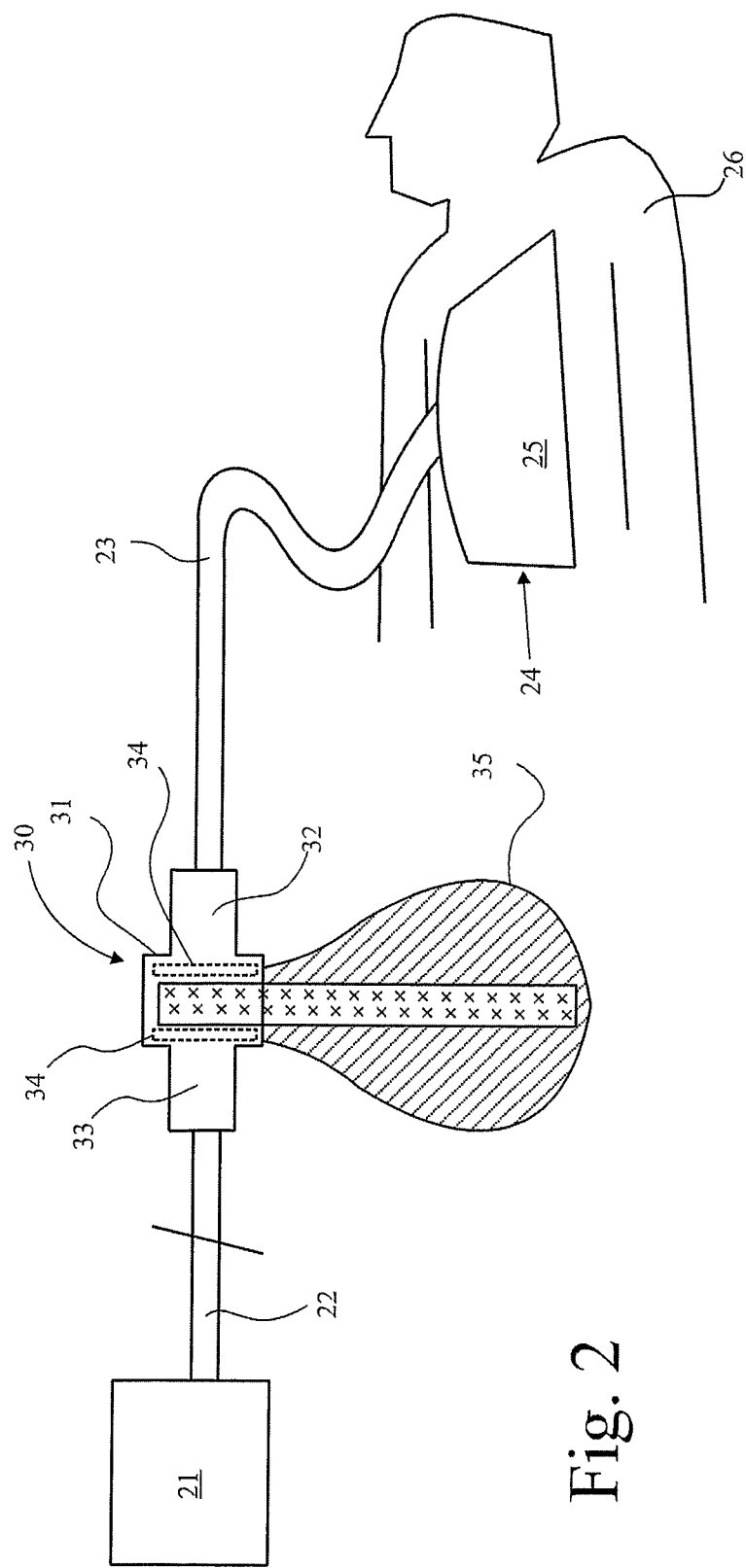
FIG. 2 illustrates apparatus being used during an NPWT procedure.

FIG. 2 illustrates an alternative embodiment of the present invention in use during a negative wound pressure therapy (NPWT) process. It is to be understood that embodiments of the present invention are broadly applicable to procedures where a discreet fluid trap and container are required. This may include, but is not restricted to, further medical procedures such as surgery, clearance of fluid from lungs or the like. Embodiments of the present invention are applicable to non-medical uses.

As illustrated in FIG. 2 a pump 21 is connected to a fluid apparatus by a pipe or tube 22 of a desired length. A further pipe or tube 23 connects the fluid trap to a target site such as a wound site 24 aptly covered by a drape 25. During a negative pressure wound therapy treatment the pump 21 continually sucks so as to apply a negative pressure at the wound site 24. The negative pressure is well known to aid healing of a wound of a user 26.

As illustrated in FIG. 2 a fluid trap 30 according to an embodiment of the present invention is located in the flow path between the pump 21 and wound site 24. The fluid trap includes a rigid body 31 which includes a fluid inlet 32 and fluid outlet 33. The fluid flowing through the inlet 32 includes a liquid and gaseous component. The fluid trap 30 traps and stores the liquid part of the input fluid whilst a remaining gaseous component is transferred through the outlet 33 to the pump and may be output via suitable filters or the like from the pump.

Unlike the embodiment illustrated with respect to FIG. 1 a screen 34 is incorporated within the body 31 to prevent migration of the super absorber material from within the flexible container 20 to the inlet or outlet. As such the upper portion of the wick 15 does not need to fill the inside of the body 31.

As illustrated in FIG. 2, during operation liquid flowing along the flow path from the target wound site 24 and pipe 23 is input into the fluid trap. The liquid contacts the upper portion of the wick 15 which transports the liquid downwardly by capillary action away from the flow path and into contact with the super absorber material stored between the wick and the inner surface of the flexible container 35. The super absorber which may be any suitable material, such as, for example, those based on polycationic or polyanionic polymers or the like is able to absorb large volumes of water with respect to dry volume of the material. Suitable superabsorbent polyanionic polymers include, but are not restricted to, polyacrylic acid salts and polyacid derivatives of polysaccharides, such as carboxyalkylcellulose, or structural derivatives. Preferably, when the material is polyanionic, it may be a polyacrylic acid salt or derivative or carboxymethylcellulose or derivative. Preferably, when the material is polycationic, it may be chitosan-based, more preferably a carboxyalkylchitosan or derivative, even more preferably carboxymethylchitosan.

Aptly suitable compositions of matter from which super-absorber can be formed are those comprised, entirely or in part, of high average molecular weight cationic polymers including zwitterionic (carrying both anionic and cationic charge) polymers with a cationic charge bias. The cationic polymer may be, or may be a derivative of, a synthetic or a naturally occurring polymer. Preferably, the cationic polymer is one carrying amine functionality. More preferably, the cationic polymer is a polysaccharide. More preferably still, the cationic polymer is chitosan or a derivative of chitosan. The chitosan may be derived from any source, marine or fungal, and is preferably of a weight average molecular weight (Mw) exceeding 10 kDa (kilodaltons), more preferably exceeding 100 kDa and most preferably exceeding 200 kDa.

Where the polymer is a derivative of chitosan, it is preferably a carboxylated derivative. More preferably, it is a carboxyalkyl derivative of chitosan. More preferably still, it is a carboxymethyl derivative of chitosan. The carboxymethyl derivative of chitosan is preferably of a weight average molecular weight exceeding 50 kDa, more preferably exceeding 100 kDa and most preferably exceeding 500 kDa.

Notably, the super absorbers are able to absorb under compression even at compression pressures of up to 200 mmHg. Thus, as the material absorbs the fluid it is able to expand in volume within the flexible container and counteract the force on the flexible container generated as a result of the interior being under partial vacuum and the exterior having the pressure of the atmosphere acting upon it.

According to embodiments of the present invention the expandable container 20, 35 may be a flexible bag. However, alternative expandable containers are envisaged according to further embodiments of the present invention.

Embodiments of the present invention obviate the need for a bulky rigid waste canister and replaces such a canister with a flexible bag or other such receptacle of only relatively small volume when empty. In order to prevent the bag completely collapsing under vacuum the bag contains wicking material and super absorbent material such that the sides of the bag are not able to wholly collapse and touch together. Thus, when operating under vacuum, fluid can enter the bag from a wound site and come into contact with the wicking material e.g. cotton gauze, non-woven polyester or the like. Liquid is trapped by the wicking layer and then rapidly transported via capillary action to the super absorbent material e.g. those noted above or the like. It is to be noted that if a puncture occurs to the expandable container the super absorbent material is such that the expandable container leaks air rather than any liquid which remains within the super absorber. This ensures the fluid trap remains hygienic.

According to embodiments of the present invention, the flexible bag may aptly have a pathogen filter on the exit port and/or a valve on the inlet port to improve control of pathogens during operation of the drainage system. In order to prevent the ports from becoming blocked before the bag is full of liquid the super absorber is prevented from migration to the port by ensuring that the rigid body is substantially full of wicking material or by the inclusion of screens around the port regions.

Embodiments of the present invention provide for a flexible waste container allowing it to be accommodated on a person in a more user friendly manner. The empty state of the waste receptacle is significantly smaller in volume (typically 10 times smaller) than an equivalent rigid container of fixed initial volume. The apparatus is thus smaller and lighter thus reducing transport and storage requirements and reducing the volume in use.

It is to be noted that the super absorber can continue to absorb and thus expand despite the negative internal pressure provided by the pump.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. Apparatus for collecting fluid, comprising:
    a body portion comprising a fluid inlet and an outlet, wherein the fluid inlet and the outlet are configured to form a fluid flow path through the body portion;
    an expandable container secured to the body portion, wherein the expandable container is adjacent to and sealed to the body portion;
    at least one wicking element comprising a first section positioned within the body portion and a second elongate section extending from within the body portion into the expandable container; and
    at least one super absorber element arranged inside the expandable container and positioned adjacent to the second elongate section of the wicking element extending from the body portion, wherein the expandable container is configured to expand in volume as liquid is absorbed by the at least one super absorber element and as a force is exerted on the expandable container as a result of an interior of the expandable container maintaining negative pressure and an exterior of the expandable container being under atmospheric pressure, wherein the at least one super absorber element is positioned away from the fluid flow path; and
    wherein the expandable container comprises an inner surface and an outer surface, the inner surface configured to be in contact with the at least one super absorber element and the liquid and the outer surface is configured to be exposed to ambient atmosphere.

2. The apparatus as claimed in claim 1 wherein the apparatus is arranged to trap and store liquid in the at least one super absorber element as fluid is drawn through the fluid inlet by a negative pressure applied at the outlet.

3. The apparatus as claimed in claim 1, wherein the at least one wicking element comprises a first portion of the at least one wicking element within the body portion and an elongate portion extending outwardly from the first portion of the at least one wicking element into the expandable container.

4. The apparatus as claimed in claim 3, wherein the elongate portion of the at least one wicking element extends substantially to a bottom region of the expandable container.

5. The apparatus as claimed in claim 3 wherein the first portion of the at least one wicking element substantially fills the body portion and is arranged to prevent migration of the at least one super absorber element to the fluid inlet or outlet.

6. The apparatus as claimed in claim 3 wherein at least one screen is located in the body portion to prevent migration of the at least one super absorber element to the fluid inlet or outlet.

7. The apparatus as claimed in claim 1, wherein the at least one super absorber element comprises a plurality of sheets of super absorbent material spaced apart in a substantially parallel arrangement and located between the at least one wicking element and the inner surface of the expandable container.

8. The apparatus as claimed in claim 1 wherein the at least one super absorber element comprises one or more of polycationic or polyanionic polymers.

9. The apparatus as claimed in claim 1 wherein the at least one wicking element comprises one or more of cotton gauze and/or non-woven polyester.

10. The apparatus as claimed in claim 1, further comprising:
    a pathogen filter located at the fluid inlet and/or outlet.

11. The apparatus as claimed in claim 1 wherein the expandable container comprises a flexible bag hermetically secured to a bottom region of the body portion.

12. A method for collecting fluid, comprising the steps of:
    applying a negative pressure at an outlet of an apparatus body portion to thereby draw liquid through an inlet of the body portion, wherein the inlet and the outlet are configured to form a fluid flow path through the body portion;
    via at least one wicking element, trapping and transporting the drawn liquid away from the body portion into an expandable container secured to the body portion, wherein the expandable container is positioned away from the fluid flow path and the expandable container is adjacent to and sealed to the body portion, and wherein the at least one wicking element comprises a first section positioned within the body portion and a second elongate section extending from within the body portion into the expandable container; and
    absorbing the liquid drawn into the expandable container via at least one super absorber element, the at least one super absorber element arranged inside the expandable container and positioned adjacent to the second elongate section of the wicking element extending from the body portion;
    wherein absorbing the liquid causes the expandable container to expand in volume as the at least one super absorber element absorbs liquid and expands and as a force is exerted on the expandable container as a result of an interior of the expandable container maintaining negative pressure and an exterior of the expandable container being under atmospheric pressure.

13. The method as claimed in claim 12, further comprising the steps of:
  absorbing liquid via the at least one super absorber element under compression conditions in the expandable container.

14. The method as claimed in claim 12, further comprising the steps of:
  preventing the at least one super absorber element from the expandable container migrating to the outlet or inlet by a first portion of the at least one wicking element substantially filling the body portion.

15. The method as claimed in claim 12, further comprising the steps of:
  preventing the at least one super absorber element from the expandable container migrating to the outlet or inlet by at least one screen located in the body portion.

16. The apparatus as claimed in claim 1, wherein the body portion comprises a rigid or semi-rigid material.

17. The apparatus as claimed in claim 1, wherein the fluid inlet is positioned on a side wall of the body portion and an outlet is positioned on an opposite side wall of the body portion.

* * * * *